United States Patent
Zhou

(10) Patent No.: US 10,525,127 B2
(45) Date of Patent: Jan. 7, 2020

(54) P14.7 PROTEIN AND USES THEREOF AS VACCINE ADJUVANT

(71) Applicant: Wenyun Zhou, San Diego, CA (US)

(72) Inventor: Wenyun Zhou, San Diego, CA (US)

(73) Assignee: Femtomab, San Diego, CA (US)

( * ) Notice: Subject to any disclaimer, the term of this patent is extended or adjusted under 35 U.S.C. 154(b) by 0 days.

(21) Appl. No.: 15/942,521

(22) Filed: Mar. 31, 2018

(65) Prior Publication Data

US 2019/0298823 A1     Oct. 3, 2019

(51) Int. Cl.
    *A61K 39/39*      (2006.01)
    *A61K 39/00*      (2006.01)
    *A61K 39/29*      (2006.01)

(52) U.S. Cl.
    CPC .......... *A61K 39/39* (2013.01); *A61K 39/0005* (2013.01); *A61K 39/292* (2013.01)

(58) Field of Classification Search
    CPC ... A61K 39/39; A61K 39/0005; A61K 39/292
    See application file for complete search history.

(56) References Cited

U.S. PATENT DOCUMENTS

| | | | | |
|---|---|---|---|---|
| 6,086,890 A | * | 7/2000 | Mittal | C07K 14/005 424/199.1 |
| 9,567,605 B2 | * | 2/2017 | Cohen | A61K 48/005 |

\* cited by examiner

*Primary Examiner* — Bao Q Li
(74) *Attorney, Agent, or Firm* — Lili Chen

(57) ABSTRACT

The present invention Provides composition and method for stimulating immune responses against antigens without using conventional adjuvants (such as aluminum salt adjuvants, oil-in-water emulsion adjuvants, toll-like receptor agonist adjuvants, and the like). The composition contains p14.7 protein and an antigen to which the stimulated illumine responses are desired. The p14.7 protein functions as an adjuvant so that the immune responses to the antigen stimulated by the composition comprising p14.7 protein and the antigen are greater than the immune responses stimulated by the antigen alone. The current invention also provides a method for producing thermostable vaccines and a simple strategy for avoiding vaccine cold-chain maintenance by lyophilization.

3 Claims, 2 Drawing Sheets

Specification includes a Sequence Listing.

Antibody Response Test

HEK293CH2CH3 stained with pre-immunization mice serum

HEK293CH2CH3 stained with mice serum immunized by CH2CH3 protein

Fig 1 Antibody Response Test

HEK293CH2CH3 stained with pre-immunization mice serum

HEK293CH2CH3 stained with mice serum immunized by CH2CH3 protein

Fig 1 Antibody Response Test

HEK293CH2CH3 stained with mice serum immunized by p14.7-CH2CH3 protein

HEK293 stained with mice serum immunized by p14.7-CH2CH3 protein

P14.7 PROTEIN AND USES THEREOF AS VACCINE ADJUVANT

FIELD OF THE INVENTION

The present invention relates to vaccines, and more particularly to vaccine adjuvant that potentiates the immune responses against antigens.

BACKGROUND OF THE INVENTION

Vaccines are among the most effective interventions in modern medicine. Ever since Edward Jenner's first use of a vaccine against smallpox in 1796, the use of vaccines has become indispensable to the eradication of disease (Gary J. Nabel, 2013). Vaccines are used to elicit the specific immune responses against a particular target antigen. For example, vaccines against viral or bacterial components are used to prevent or limit infection caused by the respective pathogen (I. P. Nascimento et al, 2012). Vaccines against tumor specific antigens or a combination of such antigens are used in the treatment of cancer (Tagliamonte M et al, 2014), However, to an unprimed immune system, target antigens are typically poor at stimulating the specific immune responses on their own, especially in vaccines where the immunizing antigen is an isolated or synthesized peptide. To overcome this, commercial vaccine preparations typically contain not just the target antigen, but also an immunological adjuvant (Alberta Di Pasquale et al, 2015).

A vaccine adjuvant is more precisely a particulate, solid or soluble agent that increases the specific immune responses to an antigen. Vaccine adjuvants can enhance the immune responses to vaccine antigens in various ways. They are very useful for augmenting the immunogenicity and vaccine potency of weak antigens. They are used to enhance the speed, vigor, and persistence of the immune responses to strong antigens. The vaccine adjuvants are useful for potentiating the immune responses in immunologically immature, immune-suppressed or senescent individuals, acting as an immunological booster. Also, the vaccine adjuvant can effectively decrease the dose of antigen and/or the frequency of injection necessary to provide protection (Robert L et al, 2010; Marciani D J, 2003).

Antigens have been combined with aluminum-containing adjuvant since 1926, when Glenny and colleagues originally precipitated diphtheria toxoids with aluminum salt and observed an unproved immune response over a soluble antigen inoculation (A. P. C. Glenny et al, 1926). The most widely used adjuvant in medicine is aluminum that is used in both human and veterinary vaccines under the form of aluminum salts. An important formulation and stability concern for vaccines with aluminum salts is their reduced efficacy following freeze-thaw stress. Exposure to freeze-thaw stress results in agglomeration of the vaccines containing aluminum salts and vaccine potency loss. In addition, whereas aluminum salts stimulate the strong immune responses to the specific antigen (Baylor N W et al, 2002), its toxic effects (neurological toxicity, autoimmunity) are well but only partially known (Kumar V et al, 2009; Shaw C A I et al, 2013). The safety of aluminum salts as a vaccine adjuvant is still being concerned (Tomljenovic L. et al, 2011).

Oil-in-water emulsions have gained interest as adjuvants on account of substantial increases in the quality of the elicited immune responses compared with traditional aluminum salts based adjuvants (G. Leroux-Roels, 2010; F. R. Vogel et al, 2009). However, most emulsions cannot be readily frozen or lyophilized, on account of the risk of phase separation, and may have a deleterious effect on protein antigen stability when stored long term as a liquid co-formulation. Typically, the protein antigen and the emulsion must be mixed together just before administration to obtain the optimal efficacy (G. L. B. Gary Ott et al, 1995).

The Toll-like receptor (TLR) adjuvant category covers an extremely broad spectrum of pathogen-derived compounds including nucleic acids, proteins, lipopeptides and glycolipids, and synthetic analogues thereof (Petrovsky N et al, 2004). Each of these types of compounds is likely to have very different toxicities. All TLR agonists activate the inflammatory transcription factor, NFkB, through the TLR adaptor proteins, MYD88 and TRIF (Verstak B et al, 2007). A consequence of NFkB activation is production of pyrogens and inflammatory cytokines. NFkB activation may be involved in the induction of chronic inflammation and autoimmune reactions (Collins S E et al, 2014; Akbar Mohammad Hosseini et al, 2015).

Many vaccines are thermally labile, which can challenge distribution and storage of vaccines in countries where cold-chain management is difficult (Brandau D T et al, 2003). The development of thermostable products can help with the distribution of vaccines in these areas, and can also help reduce waste of product that has inadvertently been stored at temperatures that exceed or fall below specified storage temperatures. At this point, lyophilization of vaccines is of great interest. Lyophilization of vaccines is advantageous for the distribution and storage of thermally labile products, particularly in regions where cold-chain management is difficult. In addition, lyophilized formats have potential to provide for longer product shelf lives. Vaccines containing aluminum salt or oil-in water emulsion adjuvants generally could not be lyophilized. To date, current lyophilized vaccines do not contain an adjuvant. Instead, adjuvanted vaccines may be presented as a two vial system, that require bedside-mixing prior to immunization.

World Health Organization (WHO) guidelines and manufacturer product inserts recommend that all vaccines except oral polio vaccine be kept at 2-8° C. during in-country distribution. This presents a significant financial and technological barrier to worldwide implementation of such vaccines. Additionally, cold-chain maintenance cannot be ensured during natural disasters when power supplies may be compromised. Development of adjuvanted vaccines that de not require cold-chain maintenance would significantly reduce the cost and technological hurdles of implementation of new vaccines worldwide, especially in low resource settings.

There is a need for developing new adjuvants which are safer and convenient to use. There is also a need for thermostable adjuvanted vaccines that are chemically stable at sustained temperatures and that retain the ability to elicit the immune responses against the vaccine antigens. As disclosed herein, the present invention meets these above-mentioned needs.

SUMMARY OF THE INVENTION

The present invention is related to a small protein (p14.7) having adjuvant properties, vaccines comprising the small protein (p14.7) adjuvant, and the use of the small protein (p14.7) adjuvant for prophylaxis or therapy purpose.

In an embodiment, in accordance with the present invention, there is provided an immunogenic composition comprising said p14.7 adjuvant protein and said antigen, or a nucleic acid encoding said p14.7 adjuvant protein and said antigen.

In an embodiment, the p14.7 adjuvant protein and the antigen are linked together, or the nucleic acid encoding said p14.7 adjuvant protein and said antigen are linked together.

In an embodiment, the present invention provides the use of an immunogenic composition comprising a p14.7 adjuvant protein and an antigen, or a nucleic acid encoding said p14.7 adjuvant protein and said antigen, for the preparation of a medicament for inducing the immune responses against said antigen in a subject.

In an embodiment, the immunogenic composition is p14.7-antigen fusion protein existing in the form of a single chain protein. The p14.7-antigen single chain protein immunogenic composition will be comparatively feasible to be lyophilized.

Other objects, advantages and features of die present invention will become more apparent upon reading of the following non-restrictive description of specific embodiments thereof, given by way of example only with reference to the accompanying drawing.

BRIEF DESCRIPTION OF THE DRAWING

FIG. 1A showing HEK293CH2CH3 cells stained with mice sera without vaccination; FIG. 1B showing HEK293CH2CH3 cells stained with mice sera vaccinated with CH2CH3 protein; FIG. 1C showing HEK293CH2CH3 cells stained with mice sera vaccinated with p14.7-CH2CH3 protein; FIG. 1D showing parental HEK293 cells stained with mice sera vaccinated with p14.7-CH2CH3 protein.

DEFINITIONS

Figure 1:
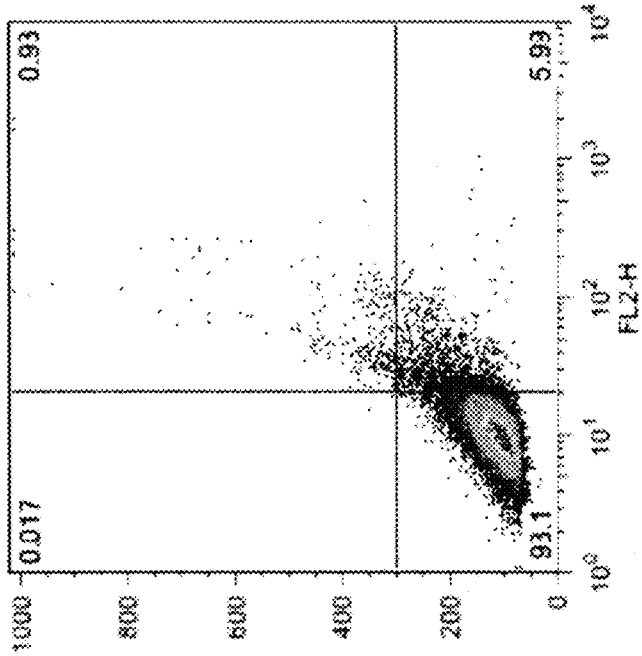
FIG. 1 showing the antibody responses in mice vaccinated with the recombinant proteins. Pcdna3-CH2CH3 plasmid was used to transfect HEK293 cells. Stable CH2CH3 protein expression cell line, named HEK293CH2CH3, was selected by G418 drug from transfected HEK293 cells. CH2CH3 is human IgG gene heavy chain constant region 2 and region 3. HEK293CH2CH3 cells were stained with different mice sera.
Figure 1:
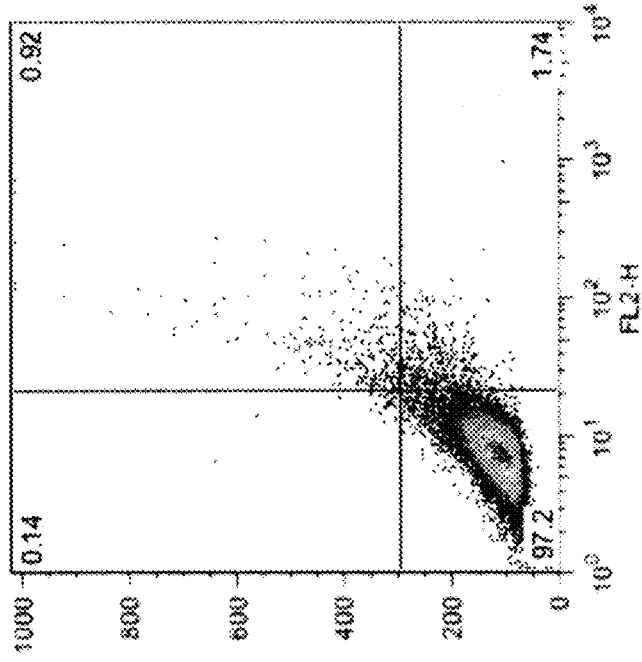
Figure 1:
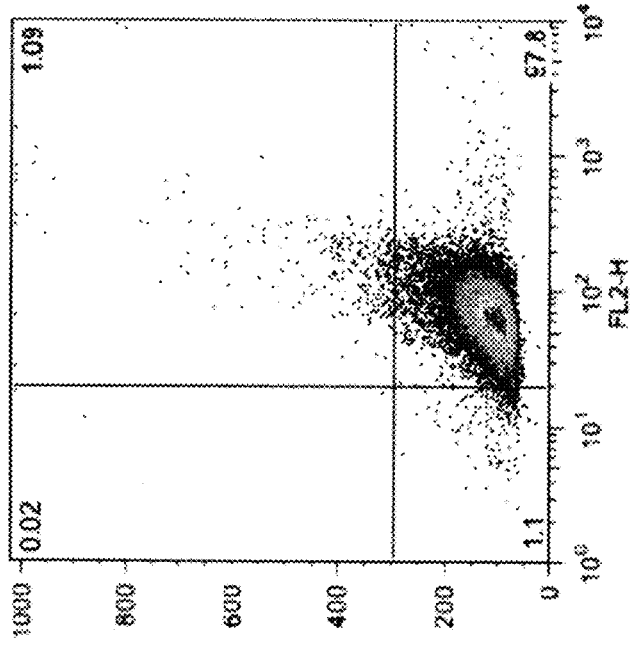
Figure 1:
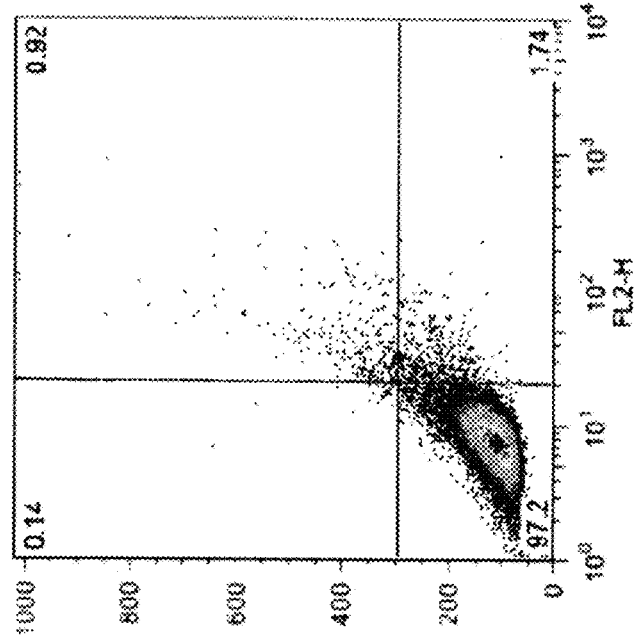

The term "vaccine" as used herein is a biological preparation that improves immunity to a particular disease. A vaccine typically contains an agent that resembles a disease-causing microorganism, and is often made from weakened or killed forms of the microbe, its toxins or one of its surface proteins.

The term "antigen" is meant a molecule that is capable of stimulating a host's immune system to make the cellular antigen-specific immune responses and/or the humoral antibody responses when the antigen is administered. Similarly, an oligonucleotide or polynucleotide that expresses an immunogenic protein, or antigenic determinant in vivo, such as in nucleic acid immunization applications, is also included in the definition of antigen herein.

"Adjuvant" refers to a substance which, when added or linked to an immunogenic agent such as an antigen, non-specifically enhances or potentiates the immune responses to the agent in the host upon exposure to the mixture. "Adjuvant" activity as used refers to the increase in the immune responses/reactions to an antigen when the antigen is used together with the adjuvant, compared with the immune responses/reactions to an antigen when the antigen is used alone.

"Variant" used herein refers to the p14.7 protein in which one or more of the amino acid(s) of the adenovirus type 5 E3 p14.7 protein, or its paralog, or its homolog, or its ortholog thereof has/have been modified, but which retains adjuvant activity. The modification may be, for example, a deletion of one or more consecutive or non-consecutive amino acids, a substitution of one or more amino acid(s), or an extension of the sequence by e.g., one, two, three or more amino acid(s).

Homolog: A gene related to a second gene by descent from a common ancestral DNA sequence. The term "homolog" may apply to the relationship between genes separated by speciation (see ortholog), or to the relationship between genes originating via genetic duplication (see paralog). The proteins encoded by the related genes can also be named as homologs.

Ortholog: Orthologs are genes in different species that have evolved from a common ancestral gene via speciation. Orthologs often (but certainly not always) retain the same function(s) in the course of evolution. Thus, functions may be lost or gained when comparing a pair of orthologs. The proteins encoded by the related genes can also be named as orthologs.

Paralog: Paralogs are genes related by duplication within a genome. Orthologs retain the same function in the course of evolution, whereas paralogy evolve new functions, even if these are related to the original one. The proteins encoded by the related genes can also be named as prologs.

DETAILED DESCRIPTION OF THE INVENTION

Terms and symbols of genetics, molecular biology, biochemistry and nucleic acid used herein follow those of standard treatises and texts in the field, e.g. Kornberg and Baker, DNA Replication, Second Edition (W. H. Freeman, New York, 1992); Lehninger, Biochemistry, Second Edition (Worth Publishers, New York, 1975); Strachan and Read, Human Molecular Genetics, Second Edition (Wiley-Liss, New York, 1999). All terms are to be understood with their typical meanings established in the relevant art.

The present invention is based on the unexpected discovery that a small p14.7 protein encoded by the E3 region of adenovirus type 5 can act as an adjuvant when linked with other antigen. The invention provides composition and method for enhancing the immune responses against an antigen in an individual. The composition comprises the p14.7 protein and an antigen. The amino acid sequence of p14.7 protein is shown in present invention as SEQ ID NO: 1. The p14.7 protein can comprise or consist of a 128 amino acid sequence, wherein the protein comprising or consisting of the 128 amino acid sequence has adjuvant activity.

In an embodiment, the p14.7 protein comprises the amino acid sequence shown for NCBI Reference Sequence: AP_000224.1. The adenovirus E3, p14.7 protein, expressed early in the life cycle of adenoviruses, inhibits cell death mediated by TNF-alpha and FasL receptors. P14.7 protein is highly oligomerized. P14.7 protein exists in a stable high-order oligomeric state (nonamer) in solution. P14.7 protein contains a proteolytically-resistant, C-terminal domain (Kim W I et al, 2002).

In an embodiment, the p14.7 adjuvant protein is incorporated into a composition together with an antigen. In an embodiment, the p14.7-encoding nucleic acid is incorporated into a composition together with the antigen-encoding nucleic acid. In an embodiment, the present invention provides the use of a p14.7 protein, or a nucleic acid encoding said p14.7 protein, as an adjuvant for a vaccine (immunogenic composition). In an embodiment, the present invention provides the use of a p14.7 adjuvant protein, or a nucleic acid encoding said p14.7 adjuvant protein, as an adjuvant for the preparation of a vaccine, in an embodiment, the vaccine further comprises an antigen, in a further embodiment a heterologous antigen.

In an embodiment, the present invention provides an immunogenic composition comprising a fusion construct, the fusion construct comprising a p14.7 adjuvant protein covalently linked to an antigen. In an embodiment, the present invention provides an immunogenic composition comprising a fusion construct, the fusion construct comprising a p14.7-encoding nucleic acid linked to an antigen-encoding nucleic acid.

In an embodiment, the above-mentioned antigen is an antigen from a human pathogen, or an antigen of human pathogen origin, or an antigen of human origin. In an embodiment, the above-mentioned antigen is an antigen from a livestock pathogen, or an antigen of livestock pathogen origin, or an antigen of livestock origin.

In an embodiment, the p14.7 adjuvant protein is (i) the protein comprising the amino acid sequence of SEQ ID NO: 1 as disclosed in the present invention and having adjuvant properties; (ii) the protein comprising a sequence that is at least 40% similar to the amino acid sequence of SEQ ID NO: 1 as disclosed in the present invention and having adjuvant properties; (iii) the fragment/variant of (i) or (ii) and having adjuvant properties. In further embodiments, the variant and/or fragment has a similarity or identity of at least 40, 45, 50, 55, 60 65, 70, 75, 80, 85, 90, 91, 92, 93, 94, 95, 96, 97, 98 or 99% with the p14.7 protein.

In an embodiment, the p14.7 adjuvant protein is (i) the homolog of SEQ ID NO: 1 as disclosed in the present invention and has adjuvant properties; (ii) the ortholog of SEQ ID NO: 1 as disclosed in the present invention and has adjuvant properties; (iii) the Paralog of SEQ ID NO: 1 as disclosed in the present invention and has adjuvant properties; (iv) the fragment/variant of (i) or (ii) or (iii) and has adjuvant properties.

In an embodiment, the adjuvant is a nucleic acid encoding the above-mentioned p14.7 adjuvant protein. In an embodiment, the nucleic acid comprises a fragment of the nucleic acid encoding p14.7 and has adjuvant c after translated into protein. In an embodiment, the nucleic acid comprises p14.7 paralog, or p14.7 homolog, or p14.7 ortholog thereof and has adjuvant activity after translated into protein.

In an embodiment, the variant and/or fragment of the nucleic acid has an identity or similarity of at least 40% with the nucleic acid encoding p14.7. In an embodiment, the variant and/or fragment of the nucleic acid has an identity or similarity of at least 40% with the nucleic acid encoding p14.7 paralog, or p14.7 homolog, or p14.7 ortholog thereof and retains adjuvant activity after translated into protein.

In embodiments, the p14.7 protein or nucleic acid may be covalently linked to the antigen either directly (e.g., through a peptide bond) or via a suitable linker moiety, e.g., a linker of one or more amino acids (e.g., a polyglycine linker) or another type of chemical linker.

In an embodiment, one or more additional peptides or polypeptides may be inserted (1) between the p14.7 protein and the antigen (2) N-terminal to the p14.7-antigen construct, and/or (3) C-terminal to the p14.7-antigen construct. In an embodiment, the p14.7 protein and the antigen are covalently linked through a peptide bond (as a fusion protein). In an embodiment, the nucleic acid encoding said p14.7 is 5' relative to the nucleic acid encoding said antigen. In an embodiment, the nucleic acid encoding said p14.7 is 3' relative to the nucleic acid encoding said antigen.

In an embodiment, the p14.7-antigen construct further comprises a domain which facilitates its purification for examples: His-tag, HA-tag, GST-tag, and the like.

A recombinant p14.7-antigen expression vector of the present invention can be constructed by standard techniques known to one of ordinary skill in the art and found, for example, in Molecular Cloning, A Laboratory Manual, 3rd edition, Cold Spring Harbour Laboratory Press, Cold Spring Harbour, N.Y. (2001).

The above description of modification of the p14.7 adjuvant protein does not limit the scope of the approaches nor the possible modifications that can be engineered.

In an embodiment, the p14.7-antigen fusion protein can be purified by many techniques well known in the art, such as reverse phase chromatography, high performance liquid chromatography (HPLC), ion exchange chromatography, size exclusion chromatography, affinity chromatography, gel electrophoresis, and the like. The actual conditions used to purify the p14.7-antigen fusion protein will depend, in part, on production strategy and on factors such as net charge, hydrophobicity, hydrophilicity, and the like, and will be apparent to those of ordinary skill in the art. For affinity chromatography purification, any antibody which specifically binds the p14.7-antigen fusion protein, or an affinity tag attached thereto, may for example be used.

The composition of the present invention may be used for both prophylactic and therapeutic purposes. Accordingly, there is provided the use of the p14.7 protein, in combination with a heterologous antigen, in the manufacture of an immunogenic composition (e.g., a vaccine) for the prophylaxis and/or the treatment of viral, bacterial, fungal, parasitic infections, allergy, cancer and other disorders in which the heterologous antigen may be useful. Accordingly, the present invention provides for a method of treating a mammal susceptible to or suffering from an infectious disease or cancer, or allergy, or autoimmune disease using the above-mentioned composition or vaccine (e.g., by administering an effective amount of the composition to a subject in need thereof). In a further embodiment of the present invention, there is provided a vaccine or immunogenic composition, comprising the p14.7-antigen fusion protein or the p14.7-antigen fusion protein encoding nucleic acid, as herein described, for use as a medicament. Immunogenic/vaccine preparation is generally described in New Trends and Developments in Vaccines, edited by Voller et al., University Park: Press, Baltimore, Md., U.S.A. 1978.

Benefits for using p14.7 protein as adjuvant: (1) p14.7 protein is a small polypeptide containing only 128 amino acids. The small p14.7 protein could be easily linked with other antigen by common genetic manipulation method; (2) p14.7 protein is like a carrier protein but has the ability to enhance immune responses against other antigen when linked with other antigen. The p14.7 peptide could replace Keyhole limpet hemocyanin (KLH) or bovine serum albumin (BSA) as a carrier protein efficiently inducing immune responses without adding conventional adjuvants, which make it more practical to be used in human or livestock immunization; (3) p14.7 is not like aluminum salt adjuvants or oil-in water emulsion adjuvants which could not be frozen or lyophilized in one vial with said antigen. The p14.7-antigen immunogenic composition existing as a single-chain protein product, without aluminum salt adjuvants or oil-in-water emulsion adjuvants, will be comparatively feasible to be lyophilized. Lyophilization of p14.7-antigen immunogenic compositions is advantageous for the distribution and storage, particularly in regions where cold-chain management is difficult; (4) Mice immunized with CH2CH3 protein or p14.7-CH2CH3 protein were in healthy states throughout the whole immunization period, which could reduce the safety concerns on using p14.7 as adjuvant; (5) The adenovirus serotype 5 is commonly used in clinical trials (Stephan A. Vorburger et al, 2002). The p14.7 protein is encoded by the E3 region of adenovirus serotype 5, which could make it approvable by Food and Drug Administration (FDA) to be used in clinical trials.

EXAMPLES

The following examples are included to demonstrate preferred embodiments of the invention. It should be appreciated by those of skill in the art that the techniques disclosed in the examples, which follow represent techniques discovered by the inventor to function well in the practice of the invention, and thus can be considered to constitute preferred modes for its practice. However, those of skill in the art should, in light of the present invention, appreciate that many changes can be made in the specific embodiments which are disclosed and still obtain a like or similar result without departing from the spirit and scope of the invention.

Plasmid DNA Constructs

The plasmid DNA construct of CH2CH3 protein expression (Pcdna3-CH2CH3, CH2CH3 is human IgG heavy chain constant region 2 and region 3) and the plasmid DNA construct of p14.7-CH2CH3 fusion protein expression (Pcdna3-p14.7-CH2CH3) described in the present invention were carried out according to the general techniques of genetic engineering and molecular cloning detailed in Molecular Cloning, A Laboratory Manual, 3rd edition, Cold Spring Harbour Laboratory Press, Cold Spring Harbour, N.Y. (2001).

Protein Production

The CH2CH3 protein and p14.7-CH2CH3 fusion protein described in the present invention were produced by CHO cells (R80007, invitrogen, Carlsbad, Calif.) according to the manufacturer's protocol. Briefly, the sequence verified plasmids (Pcdna3-CH2CH3 or Pcdna3-p14.7-CH2CH3) were used to transfect CHO cells. Transfected CHO cells were cultivated in serum-free FreeStyle™ CHO Expression Medium (Cat#1.2651-014), in an incubator at 37° C., 95% humidity and 8% CO2. Transfection was performed using the FreeStyle™ MAX Reagent (Cat#16447100, Invitrogen, Carlsbad, Calif.) according to the manufacturer's protocol. Transfected cells were incubated for 6 to 7 days on an orbital shaker platform rotating at 135 rpm. Proteins were purified by protein A agarose (Cat#20333, Thermo Fisher) according to the manufacturer's protocol.

Mice Immunization

Mice immunization was performed as described in the book (Antibodies: A Laboratory Manual, Second edition, by Ed Harlow, David P Lane, CSHL Press). Briefly, Mice were given injections of the purified proteins by intraperitoneal injection. Immunizations were performed in phosphate-buffered saline (PBS) without conventional adjuvant such as aluminum salt adjuvant: or oil-in-water emulsion adjuvant. For the initial immunization (Day 0) 50 ug of protein (CH2CH3 protein or p14.7-CH2CH3 protein) in PBS was used without mixing with any conventional adjuvants. For the boosts on days 14, and 21, 50 ug of protein (CH2CH3 protein or p14.7-CH2CH3 protein) in PBS was used without mixing with any conventional adjuvants. Test bleeds were collected 7 days after each booster immunization to monitor serum antibody levels.

Immune Responses Test

Mice immune responses to CH2CH3 protein or p14.7-CH2CH3 fusion protein was tested by Flow cytometry. Test bleeds were collected 7 days after booster immunization. Serum was collected by spinning down bleeds at 13,000 rpm for five minutes. The supernatant serum was collected and diluted at 1:20,000. HEK293CH2CH3 cells was first stained with 100 ul diluted serum and then stained with anti-mouse IgG PE second antibody (R&D Systems, cat# F0102B). Flow cytometry was performed on a FACS-Calibur apparatus. The CellQuest software was used to acquire the data (BD BioSciences, Mountain View, Calif.). FACS staining and measuring of the fluorescence intensity were performed as described in Current Protocols in Immunology (Coligan, Kruisbeek, Margulies, Shevach and Stroher, Wiley-Interscience, 2002). All flow cytometry data were analyzed with FlowJo software (TreeStar, San Carlos, Calif.). As disclosed in FIG. 1A, HEK293CH2CH3 cells, which stably express CH2CH3 protein in the cell surface, stained with pre-immunization sera showed no CH2CH3 protein specific antibody in the sera; In FIG. 1B, HEK291CH2CH3 cells stained with mice sera vaccinated with CH2CH3 protein showed little CH2CH3 protein specific antibody existence in the sera; In FIG. 1C, HEK293CH2CH3 cells stained with mice sera vaccinated with p14.7-CH2CH3 protein showed high titer CH2CH3 protein specific antibody existence in the sera; In FIG. 1D, Parental HEK293 cells stained with mice sera vaccinated with p14.7-CH2CH3 protein showed no binding activity, which indicated the CH2CH3 protein binding specificity of mice sera vaccinated with p14.7-CH2CH3 protein.

New Hepatitis B Vaccine Production and Lyophilization

Lyophilization of protein-containing pharmaceuticals such as vaccines is a commonly employed method to prolong shelf-life and increase resistance to thermal stress (Kasper et al, 2013; Wang W, 2000), however, adjuvant formulations already used in approved human vaccines such as aluminum salts or oil-in-water emulsions are particularly challenging to lyophilize. In order to generate new lyophilization-feasible Hepatitis B vaccine, the plasmid DNA construct of p14.7-HBsAg (p14.7 protein and hepatitis B surface antigen fusion expression) could be carried out according to the general techniques of genetic engineering and molecular cloning. Production and purification of p14.7-HBsAg vaccine protein could be performed according to the U.S. Pat. No. 5,242,812 A (Method for production and purification of hepatitis B vaccine). The purified p14.7-HBsAg fusion protein does not need to be formulated with aluminum salt adjuvants because p14.7 protein fragment alone in the new Hepatitis B vaccine would have strong adjuvant activity. The p14.7-HBsAg protein could be directly lyophilized to produce vaccine in the form of one vial because this immunogenic composition is purely a single chain protein without aluminum salt adjuvants or oil-in water emulsion adjuvants. The stability concern for old version of Hepatitis B vaccines with aluminum salt adjuvants is their reduced efficacy following freeze-thaw stress. The stability of new version of Hepatitis B vaccine would be improved by lyophilizing pure p14.7-HBsAg fusion protein without formulating with aluminum salt adjuvants or oil-in-water emulsions. In addition, the safety concern for using aluminum salt adjuvants as a vaccine adjuvant is not necessary when using only pure p14.7-HBsAg fusion protein as Hepatitis B vaccine. Lyophilization of new version of Hepatitis B vaccine in the form of one vial is advantageous for the distribution and storage, particularly in regions where cold-chain management is difficult.

All other subunit vaccines, such as anthrax vaccine, pertussis vaccine, could also be produced and lyophilized according to the principle of new Hepatitis B vaccine production as disclosed herein, as long as the vaccines only contain the p14.7-antigen fusion proteins.

REFERENCES

Gary J. Nabel, Designing Tomorrow's Vaccines. N Engl J Med 2013; 368:551-560.

I. P. Nascimento and L. C. C. Leite. Recombinant vaccines and the development of new vaccine strategies. Braz J Med Biol. Res. 2012 December; 45(12): 1102-1111.

Tagliamonte M, Petrizzo A, Tornesello M L, Buonaguro F M, Buonaguro L. Antigen-specific vaccines for cancer treatment. Hum Vaccin Immunother. 2014; 10 (10:3332-46.

Alberta Di Pasquale, Scott Preiss, Fernanda Tavares Da Silva, and Nathalie Garcon. Vaccine Adjuvants: from 1920 to 2015 and Beyond. Vaccines (Basel), 2015 June; 3(2): 320-343.

Robert L. Coffman, Alan Sher, and Robert A. Seder. Vaccine Adjuvants: Putting Innate Immunity to Work. Immunity. 2010 Oct. 29; 33(4): 492-503.

Marciani D J. Vaccine adjuvants: role and mechanisms of action in vaccine immunogenicity. Drug Discov Today. 2003 Oct. 15; 8(20):934-43.

A. P. C. Glenny, H. Waddington, U. Wallace The antigenic value of toxoid precipitated by potassium alum J Pathol Bacteria 29 (1926), pp. 38-45.

Baylor N W, Egan W, Richman P. Aluminum salts in vaccines-US perspective. Vaccine. 2002; 20 (Suppl 3): S18-23.

Kumar V, Gill K D. Aluminum neurotoxicity: neurobehavioural and oxidative aspects. Arch Toxicol. 2009; 83: 965-78.

Shaw C A L, Tomljenovic L. Aluminum in the central nervous system (CNS): toxicity in humans and animals, vaccine adjuvants, and autoimmunity. Immunol Res. 2013 July; 56(2-3):304-16.

Tomljenovic L, Shaw C A. Aluminum vaccine adjuvants: are they safe? Curr Med Chem. 2011: 18:2630-7.

G. Leroux-Roels Unmet needs in modern vaccinology: adjuvants to improve the immune response Vaccine, 28 (Suppl 3) (2010), pp. C25-C36.

F. R. Vogel, C. Caillet, I. C. Kusters, J. Haensler Emulsion-based adjuvants for influenza vaccines Expert Rev Vaccin, 8 (4) (2009), pp. 483-492.

G. L. B. Gary Ott, D. Chernoff, R. Radhakrishnan, P. van Hoogevest, G. Van Nest Vaccine design: the subunit and adjuvant approach Springer, New York (1995), p. 277.

Petrovsky N, Aguilar J C (2004) Vaccine adjuvants: current state and future trends En ell Biol 82: 488-496.

Verstak B, Hertzog P, Mansell A. Toll-like receptor signaling and the clinical benefits that lie within. Inflammation research: official journal of the European Histamine Research Society [et al] 2007 January; 56(1):1-1.0.

Collins S E, Mossman K L. Danger, diversity and priming in innate antiviral immunity. Cytokine & growth factor reviews. 20.14 October; 25(5):525-531.

Akbar Mohammad Hosseini, Jafar Majidi, Behzad Baradaran, and Mehdi Yousefi, Toll-Like Receptors in the Pathogenesis of Autoimmune Diseases Adv Pharm Bull. 2015 December; 5 (Suppl 1): 605-614.

Brandau D T, Jones L S, Wiethoff C M, Rexroad J, Middaugh C R (2003) Thermal stability of vaccines. Pharm Sci 92(2):218-231.

Kim H J I, Foster M P. Characterization of Ad5 E3-14.7K, an adenoviral inhibitor of apoptosis: structure, oligomeric state, and metal binding. Protein Sci. 2002 May; 11(5): 1117-28.

Stephan A. Vorburger and Kelly K. Hunt. Adenoviral Gene Therapy. The Oncologist February 2002 vol. 7 no. 1 46-59.

Kasper J C, Winter G, Friess W. Eur J Pharm Biopharm. Recent advances and further challenges in lyophilization. 2013 October; 85(2):162-9.

Wang W. Lyophilization and development of solid protein pharmaceuticals. Int J Pharm. 2000 Aug. 10; 203(1-2):1-60.

```
P14.7 amino acid sequence
                                SEQUENCE ID NO 1
M T D T L D L E M D G I I T E Q R L L E R R R A A
A E Q Q R M N Q E L Q D M V N L H Q C K R G I F C
L V K Q A K V T Y D S N T T G H R L S Y K L P T K
R Q K L V V M V G E K P I T I T Q H S V E T E G C
I H S P C Q G P E D L C T L I K T L C G L K D L I
P F N
```

The invention claimed is:

1. An immunogenic composition comprising a fusion protein of p14.7 protein of SEQ ID NO:1 and a heterologous antigen, wherein said p14.7 protein and said heterologous antigen are directly or indirectly linked together, and wherein said p14.7 protein acts as an adjuvant to increase the immunogenicity of said heterologous antigen.

2. The immunogenic composition of claim 1, wherein said heterologous antigen is an antigen from a human pathogen, an antigen of human pathogen origin, an antigen of human origin, an antigen from a livestock pathogen, an antigen of livestock pathogen origin, or an antigen of livestock origin.

3. A nucleic acid that encodes the immunogenic composition of claim 1.

* * * * *

SEQUENCE LISTING

```
<160> NUMBER OF SEQ ID NOS: 1

<210> SEQ ID NO 1
<211> LENGTH: 128
<212> TYPE: PRT
<213> ORGANISM: Adenovirus type 5

<400> SEQUENCE: 1

Met Thr Asp Thr Leu Asp Leu Glu Met Asp Gly Ile Ile Thr Glu Gln
1               5                   10                  15

Arg Leu Leu Glu Arg Arg Arg Ala Ala Ala Glu Gln Gln Arg Met Asn
            20                  25                  30

Gln Glu Leu Gln Asp Met Val Asn Leu His Gln Cys Lys Arg Gly Ile
        35                  40                  45

Phe Cys Leu Val Lys Gln Ala Lys Val Thr Tyr Asp Ser Asn Thr Thr
    50                  55                  60
```

-continued

```
Gly His Arg Leu Ser Tyr Lys Leu Pro Thr Lys Arg Gln Lys Leu Val
 65              70                  75                  80

Val Met Val Gly Glu Lys Pro Ile Thr Ile Thr Gln His Ser Val Glu
             85                  90                  95

Thr Glu Gly Cys Ile His Ser Pro Cys Gln Gly Pro Glu Asp Leu Cys
            100                 105                 110

Thr Leu Ile Lys Thr Leu Cys Gly Leu Lys Asp Leu Ile Pro Phe Asn
            115                 120             125
```